United States Patent [19]

Buckle et al.

[11] 4,263,309

[45] Apr. 21, 1981

[54] POLYCYCLIC TRIAZOLES USED TO INHIBIT ALLERGIC RESPONSES

[75] Inventors: Derek R. Buckle, Redhill; Harry Smith, Maplehurst, near Horsham, both of England

[73] Assignee: Beecham Group Limited, England

[21] Appl. No.: 953,464

[22] Filed: Oct. 23, 1978

[30] Foreign Application Priority Data

Jul. 22, 1977 [GB] United Kingdom ............... 30766/77
Nov. 10, 1977 [GB] United Kingdom ............... 46765/77
Nov. 10, 1977 [GB] United Kingdom ............... 46767/77

[51] Int. Cl.³ .................... A61K 31/41; C07D 249/00
[52] U.S. Cl. ..................................... 424/269; 548/259
[58] Field of Search ................... 424/269; 260/308 B; 548/259

[56] References Cited

U.S. PATENT DOCUMENTS

| | | | |
|---|---|---|---|
| 2,879,274 | 3/1959 | Scalera et al. | 260/308 B |
| 3,198,795 | 8/1965 | Lindsay et al. | 260/308 B X |
| 3,294,812 | 12/1966 | Mosby | 260/30 X |

*Primary Examiner*—Leonard Schenkman
*Attorney, Agent, or Firm*—Jacobs & Jacobs

[57] ABSTRACT

Compounds of formula (I):

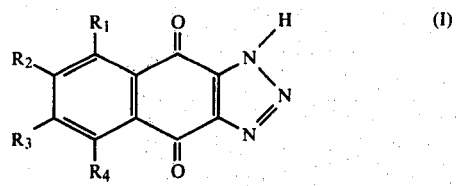

and pharmaceutically acceptable salts thereof wherein $R_1$, $R_2$, $R_3$ and $R_4$ which may be the same or different, represent hydrogen, halogen, nitro, lower alkyl, or lower alkoxy, or any adjacent two of $R_1$ to $R_4$ taken together represent an alkylene group containing from 3 to 5 carbon atoms or a 1,4-buta-1,3-dienylene group are disclosed together with a method for their preparation. The compounds are useful as anti-allergic agents. With the exception of 4,9-dioxo-1H-naphtho-[2,3-d]-triazole, and its salts, all compounds of formula (I) are novel.

5 Claims, No Drawings

POLYCYCLIC TRIAZOLES USED TO INHIBIT ALLERGIC RESPONSES

This invention relates the use of certain 4,9-dihydro-4,9-dioxo-1H-naphtho[2,3-d]-triazoles in the treatment of allergic diseases, to pharmaceutical compositions comprising these compounds to certain novel compounds within this class and to a process for their preparation.

It is generally recognised that certain cells e.g. mast cells are activated by antibody-antigen combinations and release substances such as histamine and SRS-A, which mediate an allergic response. We have discovered that 4,9-dihydro-4,9-dioxo-1H-naphtho[2,3-d]-triazoles of formula (I):

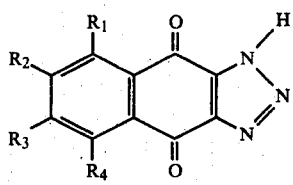

and pharmaceutically acceptable salts thereof wherein $R_1$, $R_2$, $R_3$, and $R_4$ which may be the same or different, represent hydrogen, halogen, nitro, lower alkyl or lower alkoxy, or any adjacent two of $R_1$ to $R_4$ taken together represent an alkylene group containing from 3 to 5 carbon atoms or a 1,4-buta-1,3-dienylene group, inhibit this type of antigen-induced response in mammals, and are therefore of value in the prophylaxis of diseases in which the symptoms are controlled by mediators of the allergic response. Examples of such diseases include bronchial asthma, rhinitis, hayfever and allergic eczema.

Not all the compounds of the class are novel: 4,9-dihydro-4,9-dioxo-1H-naphtho[2,3-d]triazole is known, and listed below are a number of literature references each of which discloses a different method by which the compound may be prepared.

K. Fries, R. Walter and K. Schilling, *Annalen* 576 248 (1935). L. F. Fieser and E. L. Martin, *J. Amer. Chem. Soc.* 57 1844 (1935). W. L. Mosby and M. L. Silva, *J. Chem. Soc.* 1003 (1965).

It has never been reported or suggested in the literature that the compound would have any type of pharmacological activity.

Accordingly in its broadest aspect, a method for the prophylaxis of allergic diseases which method comprises administering to a patient an effective amount of a compound of formula (I) as defined above or a pharmaceutically acceptable salt thereof.

By lower alkyl and lower alkoxy, in this specification we mean such groups containing up to six carbon atoms.

In formula (I) examples of suitable lower alkyl groups include methyl, ethyl and n-propyl.

Examples of suitable lower alkoxy groups include methoxy, ethoxy and n-propoxy.

Examples of suitable halogens include fluorine and chlorine.

The alkylene groups which any two of $R_1$ to $R_4$ may together represent are propylene, butylene and pentylene.

Where compounds of formula (I) are highly substituted, it is appreciated that substituents $R_1$ to $R_4$ are selected for steric compatibility.

The triazole moiety of the compounds of formula (I) has an acidic hydrogen, and accordingly may form salts. Examples of pharmaceutically acceptable salts falling within the scope of this invention include aluminium, alkali metal and alkaline earth metal salts such as the sodium, potassium and magnesium salt; and salts with organic bases such as amines or amino compounds including physiologically active amines such as (−) ephedrine. The sodium and ephedrine salts (−) are preferred.

Compounds of general formula (I) in which at least one of $R_1$ to $R_4$ is other than hydrogen, are novel and accordingly in a further aspect the invention provides a compound of formula (I):

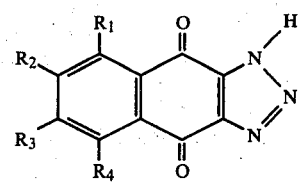

and pharmaceutically acceptable salts thereof wherein $R_1$, $R_2$, $R_3$ and $R_4$ which may be the same or different, represent hydrogen, halogen, nitro, lower alkyl or lower alkoxy, or any adjacent two of $R_1$ to $R_4$ taken together represent an alkylene group containing from 3 to 5 carbon atoms or a 1,4-buta-1,3-dienylene group, provided that $R_1$ to $R_4$ do not all represent hydrogen.

Within this group of novel compounds there are a variety of sub-groups. One group is that in which at least one of $R_1$ to $R_4$ is hydrogen and the remainder are as previously defined. An example of such a compound is 4,9-dihydro-6,7-dimethyl-5-nitro-4,9-dioxo-1H-naphtho-[2,3-d]-triazole. A further group is one where two of $R_1$ to $R_4$ are hydrogen and the remainder are as previously defined. An example of such a compound is 4,9-dihydro-5,6-dimethyl-4,9-dioxo-1H-naphtho-[2,3-d]-triazole. One preferred sub-group of compounds of formula (I) is that in which $R_1$ and $R_4$ are hydrogen and $R_2$ and $R_3$, which may be the same or different, represent methyl, ethyl or n-propyl.

An example of one such compound is: 4,9-dihydro-6,7-dimethyl-4,9-dioxo-1H-naphtho-[2,3-d]-triazole, which together with its sodium salt, constitutes the preferred embodiment of this invention.

The compounds of formula (I) above and pharmaceutically acceptable salts thereof may be prepared by a number of different methods.

The first such method comprises oxidizing a naphthotriazole of formula (II):

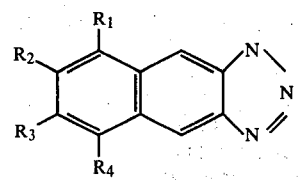

wherein $R_1$, $R_2$, $R_3$ and $R_4$ are as defined with reference to formula (I) with a powerful oxidizing agent, and thereafter optionally converting the compound of formula (I) into a pharmaceutically acceptable salt.

Suitable oxidizing agents include chromium trioxide and chromic acid. The method is carried out in a manner analogous to that described by K. Fries, R. Walter and K. Schilling, *Annalen* 576, 248, (1935); for the preparation of 4,9-dihydro-4,9-dioxo-1H-naphtho-[2,3-d]-triazole.

A second method comprises deamination of a 2-amino-naphtho-triazole (III):

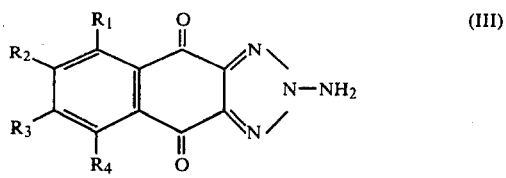
(III)

wherein $R_1$, $R_2$, $R_3$, and $R_4$ are as defined with reference to formula (I) above, with nitrous acid, and thereafter optionally converting the compound of formula (I) into a pharmaceutically acceptable salt thereof.

The method is carried out in a manner analogous to that described by W. L. Mosby and M. L. Silva, *J. Chem. Soc.*, 1003, (1965), for the preparation of 4,9-dihydro-4,9-dioxo-1H-naphtho[2,3-d]-triazole.

However, we have found that compounds of formula (I) above are most conveniently made by a process which comprises reacting a compound of formula (IV):

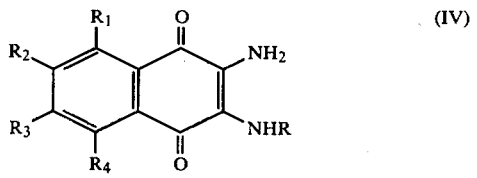
(IV)

wherein $R_1$, $R_2$, $R_3$ and $R_4$ are as defined with reference to formula (I) and R is hydrogen or an acyl group, with nitrous acid, and thereafter optionally converting the compound of formula (I) into a pharmaceutically acceptable salt.

Suitable acyl groups include benzoyl and lower alkanoyl. Examples of suitable lower alkanoyl groups are acetyl, propionyl and butyryl.

The nitrous acid is most suitably generated in situ from an alkali metal nitrite and an acid.

Most suitably the alkali metal nitrite is sodium nitrite, and the acid is a mineral acid such as hydrochloric acid.

The reaction is carried out in a solvent which is inert to the reagents and products. Examples of such solvents include water and acetic acid.

We have found water to be most convenient.

The reaction should be carried out at room temperature or below i.e. preferably between 0° C. and 25° C.

The preparation of the compounds (I) from the quinone intermediates (IV) is facilitated by reducing the quinone to the corresponding hydroquinone, (IVa):

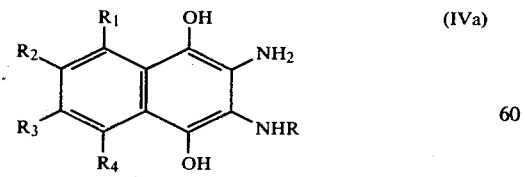
(IVa)

wherein R and $R_1$ to $R_4$ are as defined with reference to formula (IV) above and reacting the hydroquinone (IVa) with nitrous acid. These are generally more soluble in acid media than the quinones. The reduction may be carried out using any standard method for reducing quinones to hydroquinones. We have found sodium dithionite to be a most convenient reducing agent for this purpose. The hydroquinones (IVa) oxidize to the parent quinone during the reaction with nitrous acid.

Naphthotriazoles of this invention having at least one nitro substituent may be prepared by direct nitration of an appropriate triazole.

In a further aspect the invention provides a process for preparing a compound of formula (Ia):

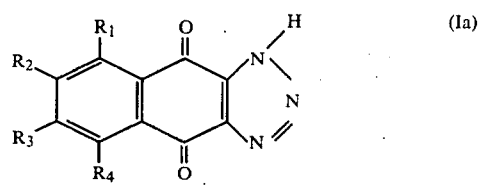
(Ia)

and pharmaceutically acceptable salts thereof; wherein $R_1$, $R_2$, $R_3$ and $R_4$ which may be the same or different represent hydrogen, halogen, nitro, lower alkyl and lower alkoxy, or any adjacent two of $R_1$ to $R_4$ taken together represent an alkylene group containing from 3 to 5 carbon atoms or a 1,4-buta-1,3-dienylene group, provided that at least one of $R_1$ to $R_4$ represent nitro which process comprises nitrating a compound of formula (Ib):

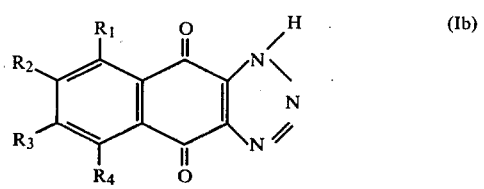
(Ib)

wherein $R_1$, $R_2$, $R_3$ and $R_4$, which may be the same or different, represent hydrogen, halogen, nitro, lower alkyl or lower alkoxy, or any adjacent two of $R_1$ to $R_4$ taken together represent an alkylene group containing from 3 to 5 carbon atoms or a 1,4-buta-1,3-dienylene group, provided that at least one of $R_1$ to $R_4$ represents hydrogen.

The reaction is carried out with a conventional nitrating agent under conventional reaction conditions. For convenience we choose to carry out the reaction with fuming nitric acid and concentrated sulphuric acid. Equally, the nitration step could be carried out with other standard reagents.

The choice of temperature at which the reaction is carried out is dependent upon the reactivity and sensitivity of the starting materials. Thus compounds which do not decompose to any significant extent may be nitrated rapidly at high temperatures for example up to 120° C., 100° C. being generally convenient. More sensitive compounds require more prolonged reaction times at lower temperatures. The time for which a reaction should be allowed to proceed depends upon the starting materials, nitrating agent and temperature but may be determined by routine procedures e.g. by following the course of the reaction by thin layer chromatography.

The synthetic route to the intermediates (IV) is summarised in the following scheme in which R, $R_1$, $R_2$, $R_3$ and $R_4$ are as defined with reference to formula (IV) above, and X is chlorine or bromine and R is an acyl group as discussed above with reference to (IV).

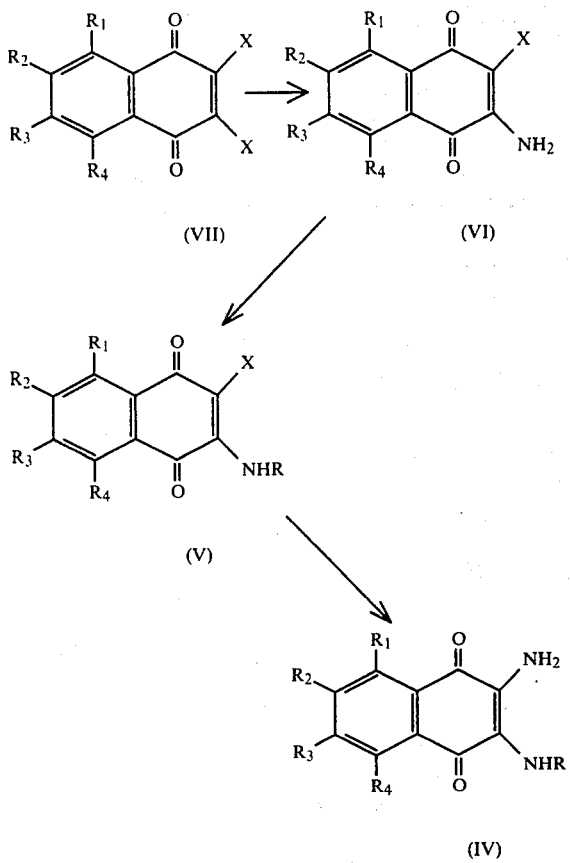

The intermediate (IV) is prepared by displacement of halogen from the corresponding 2-acylamino-3-halonaphtho-1,4-quinone (V) using ammonia and where desired thereafter removing the acyl group.

The reaction is carried out by passing dry ammonia into a solution of the compound (V) in a high boiling aprotic organic solvent which is inert to the reagent and products. Examples of such solvents include nitrobenzene, N,N-dimethylformamide and hexamethylphosphoramide. Preferably the solvent is nitrobenzene. Suitably the reaction is carried out at elevated temperatures (i.e. 80°–180° C.).

The 2-acylamino-3-halonaphtho-1,4-quinones (V) are prepared by reacting an active N-acylating derivative of benzoic or a lower alkanoic acid R -OH with a 2-amino-3-halonaphthoquinone (VI). Suitable N-acylating derivatives include the acid halide and the acid anhydride. This reaction is generally carried out in the absence of solvent in the presence of an excess of the N-acylating derivative. If desired, the reaction may be carried out in a polar organic solvent which is inert to the reagents and products. Examples of such solvents include pyridine and acetic acid.

The reaction is also suitably carried out at moderate temperature i.e. less than 100° C., room temperature being most convenient. In order to facilitate the reaction, a small amount of mineral acid may be added as a catalyst.

The 2-amino-3-halo-1,4-naphthoquinones (VI) are prepared by reacting the corresponding 2,3-dihalo-1,4-naphthoquinone (VII) with ammonia. This reaction is performed by passing dry ammonia into a solution of the compound (VII) in a high boiling aprotic organic solvent which is inert to the reagents and products, as described for the conversion of (V) to (VI) above.

Preferably the solvent is nitrobenzene. Suitably the reaction is carried out at elevated temperatures i.e. 80°–180° C.

The 2,3-dihalo-1,4-naphthoquinones (VII) are prepared from the corresponding naphthoquinones by a conventional halogenation reaction.

In order to use compounds of formula (I) or salts thereof for medical purposes, they are formulated in accordance with standard pharmaceutical practice as pharmaceutical compositions.

The invention further provides pharmaceutical compositions comprising a compound of formula (I) above or a pharmaceutically acceptable salt thereof together with a pharmaceutically acceptable carrier.

Compounds of formula (I) may be administered topically or systemically. In accordance with usual pharmaceutical procedure, the active material will be purified so as to contain minimum amounts of by-products or other impurities.

Topical formulations for administration to the skin include lotions and creams. Topical formulations for administration to the respiratory tract include solutions for application via a nebulizer or as an aerosol, snuffs and microfine insufflatable powders. The active ingredient in an insufflatable powder has a small particle size i.e. less than 50 microns and preferably less than 10 microns. The active material is co-presented with a solid carrier such as lactose which has a particle size of less than 50 microns. Insufflatable compositions in particular will be rendered substantially free of microbial contaminant.

Systemic administration may be achieved by rectal, oral or parenteral administration. A typical suppository formulation comprises the active compound with a binding and or lubricating agent such as gelatin or cocoa butter or other low melting vegetable waxes or fats. Typical parenteral compositions comprise a solution or suspension of the active material in a sterile aqueous carrier or parenterally acceptable oil.

Compounds of formula (I) which are active when given orally may be compounded in the form of syrups, tablets, capsules and lozenges. A syrup formulation will generally consist of a suspension or solution of the compound in a suitable liquid carrier such as ethyl alcohol, glycerine or water with a flavouring or colouring agent. Where the composition is in the form of a capsule, the solid is granular form optionally with a binding agent is encapsulate in an edible shell e.g. of gelatin. Where the composition is in the form of a tablet, any suitable pharmaceutical carrier routinely used for preparing solid formulations may be used. Examples of such carriers include magnesium stearate, starch, lactose, glucose, sucrose, rice flour and chalk. Preferably the composition is in unit dose form such as a pill, capsule or metered aerosol so that the patient may administer to himself a single dose.

Where appropriate, small amounts of anti-asthmatics and bronchodilators for example sympathomimetic amines such as isoprenaline, isetharine, salbutamol, phenylephrine and ephedrine; xanthine derivatives such as theophylline and aminophylline; and corticosteroids such as prednisolone and adrenal stimulants such as ACTH may be included. As is common practice, the compositions will usually be accompanied by written or printed directions for use in the medical treatment concerned, in this case as an anti-allergic agent for treatment of, for example, asthma, hay-fever or rhinitis.

The following examples illustrate the invention.

EXAMPLE 1

(a) 2-Amino-3-bromo-6,7-dimethyl-1,4-naphthoquinone

Dry ammonia was passed through a refluxing solution of 2,3-dibromo-6,7-dimethyl-1,4-naphthoquinone (10 g; mp 237°–238° C.) in dry nitrobenzene (65 ml) for 30 mins. and the orange solid which separated on cooling was filtered off and washed with light petroleum. After removal of ammonium bromide with water, 6.96 g. (86%) of material of mp 228° C. was obtained. Recrystallisation from glacial acetic acid gave analytically pure material of the same melting point. $\nu$ max(mull) 3400, 3300, 1680, 1610, 1585, 1570 cm$^{-1}$. $\delta$(DMSO) 2.35 (6H,s); 7.35 (2H, exchangeable broad singlet); 7.74 (2H,s). (Found; C, 51.50; H, 3.38; N, 4.79; $C_{12}H_{10}BrNO_2$ requires; C, 51.45; H, 3.60; N, 5.00%).

(b) 2-Acetamido-3-bromo-6,7-dimethyl-1,4-naphthoquinone 10 g. of 2-amino-3-bromo-6,7-dimethyl-1,4-naphthoquinone were dissolved in acetic anhydride (100 ml) containing a few drops of concentrated sulphuric acid and the yellow acetyl derivative which separated with filtered off and dried to give 9.0 g of crude product. Recrystallisation from chloroform-petrol gave 7.75 g (67%) of material of mp 252° C. $\nu$ max(mull) 3210, 1685, 1665, 1600 cm$^{-1}$; $\delta$ DMSO) 2.11(3H,s); 2.38 (6H,s); 7.80 (1H,s); 7.85 (1H,s), 1 low field exchangeable proton (Found; C, 50.98; H, 3.76; N, 4.30; $C_{14}H_{12}BrNO_3$ requires; C, 52.03; H, 3.74; N, 4.33%).

(c) 2-Acetamido-3-amino-6,7-dimethyl-1,4-naphthoquinone

Dry ammonia was passed through a stirred refluxing solution of 2-acetamido-3-bromo-6,7-dimethyl-1,4-naphthoquinone (7.5 g) in nitrobenzene (50 ml) for 1 hr. and the mixture cooled. The red solid which separated was filtered off, washed well with ether-petrol and then water to give 4.46 g. (77%) of material of mp 212°–216° C. Recrystallisation from ethanol raised the melting point to 216° C., $\nu$ max(mull), 3400, 3270, 1675, 1665, 1630 cm$^{-1}$. $\delta$ (DMSO) 2.05 (3H,s); 2.35 (6H,s); 6.64 (2H, exchangeable s); 7.71(2H,s); 9.00 (1H, exchangeable s.) (Found; C, 65.07; H, 5.43; N, 10.66; $C_{14}H_{14}N_2O_3$ requires; C, 65.10; H, 5.46; N, 10.85%).

(d) 4,9-dihydro-6,7-dimethyl-4,9-dioxo-1H-naphtho[2,3-d]-triazole

Sodium dithionite (2.5 g) in water (10 ml) was added to 2-acetamido-3-amino-6,7-dimethyl-1,4-naphthoquinone (1.68 g) in water (150 ml) and the stirred suspension left for 1 hr. The white hydroquinone which formed was filtered off and added to 2 N HCl (50 ml). The solution was cooled to 0° C. and a solution of sodium nitrite (2 g) in water (20 ml) was added over 2 hrs. The suspension which formed was stirred overnight at room temperature and the white product filtered off to give 1.34 g (84%) of material of mp 262° C. (dec) which was shown to be a monohydrate, $\nu$ max(mull) 3590, 3420, 1700, 1665, 1595 cm$^{-1}$. After recrystallisation from acetone-water and drying under vacuum at 107° C., the anhydrous material was isolated, $\nu$ max(mull) 3120, 1695, 1675, 1595 cm$^{-1}$. $\delta$ (DMSO) 2.22 (6H,s); 7.56 (2H,s); 1 low field broad exchangeable proton. (Found; C, 63.20; H, 3.96; N, 18.33; $C_{12}H_9N_3O_2$ requires C, 63.44, H, 3.99; N, 18.50%).

EXAMPLE 2

(a) 2-Amino-3-bromo-6(7)-methyl-1,4-naphthoquinone

Dry ammonia was passed through a stirred, refluxing solution of 2,3-dibromo-6-methyl-1,4-naphthoquinone (12.3 g, mp. 192° C.) in dry nitrobenzene (75 ml) for 1 hr. The red solid which separated on cooling was filtered off, washed well with petroleum ether (bp. 40–60) and water and recrystallised from glacial acetic acid to give 7.5 g. (75%) of material of mp 173° C. (Found; C, 49.78; H, 3.23; N, 5.08; $C_{11}H_8BrNO_2$ requires; C, 49.65; H, 3.03; N, 5.26%).

(b) 2-Acetamido-3-bromo-6(7)-methyl-1,4-naphthoquinone

Acetylation of 2-amino-3-bromo-6(7)-methyl-1,4-naphthoquinone (7.5 g) as described in Example 1b afforded 6.0 g (70%) of the 2-acetamido derivative of mp 192°–193° C. (Found; C, 49.51; H, 3.23; Br, 25.59; N, 4.16; $C_{13}H_{10}BrNO_3$ requires; C, 50.67; H, 3.27; Br, 25.93; N, 4.54%)

(c) 2-Acetamido-3-amino-6(7)-methyl-1,4-naphthoquinone

Dry ammonia was passed through a stirred refluxing solution of 2-acetamido-3-bromo-6(7)-methyl-1,4-naphthoquinone (6 g) in nitrobenzene (50 ml) for 1 hr. and the product worked up as in example 1c to give 1.7 g (40%) of title compound of mp (EtOH) 200°–201° C. (Found; C, 63.80; H, 4.92; N, 11.16; $C_{13}H_{12}N_2O_3$ requires; C, 63.93; H, 4.95; N, 11.47%).

(d) 4,9-Dihydro-4,9-dioxo-6methyl-1H-naphtho[2,3-d]-triazole 1.6 g of 2-acetamido-3-amino-6(7)-methyl-1,4-naphthoquinone was converted into the title triazole by the procedure outlined in example 1d. Yield 0.75 g (51%) mp (aqueous acetone) 235° (dec). (Found; C, 57.25; H, 3.77; N, 18.00; $C_{11}H_7N_3O_2.H_2O$ requires; C, 57.07; H, 3.92; N, 18.27%).

EXAMPLE 3

(a) 2,3-Dibromo-6-methoxynaphtho-1,4-quinone

Bromine (25.4 g) was added to a stirred mixture of 6-methoxynaphtho-1,4-quinone (15.1 g, 0.08 mole) and anhydrous sodium acetate (13.3 g) in chloroform (125 ml) and the mixture stirred at room temperature for 3 days. After filtration the resulting liquid was evaporated to a dark solid, 23.2 g (84%) which after recrystallization from petroleum ether (b.p. 60°–80° C.) had mp 146°–148° C. (Found; C, 38.33; H, 1.70; Br, 46.72; $C_{11}H_6Br_2O_3$ requires; C, 38.19; H, 1.75; Br, 46.19%).

(b) 2-Amino-3-bromo-6(7) methoxynaphtho-1,4-quinone

Dry ammonia was passed through a stirred, refluxing solution of 2,3-dibromo-6-methoxynaphtho-1,4-quinone (9.7 g, 0.028 mole) in N,N-dimethylformamide (80 ml) for 45 min. and the cooled mixture poured into water. The red solid which separated was filtered off, washed well with water and dried to give 7.34 g (93%) of product which had mp. (EtOH/H₂O) 184° C. (dec).

(c) 2-Acetamido-3-bromo-6(7-)-methoxynaphtho-1,4-quinone

Concentrated sulphuric acid (2 drops) was added to a suspension of 2-amino-3-bromo-6(7)-methoxynaphtho-1,4-quinone (3.6 g, 0.0125 mole) in acetic anhydride (30 ml) and the dark mixture stirred for 15 min. After pouring into water an olive green solid separated which was filtered off and recrystallized from ethanol containing charcoal to give 3.4 g (84%) of a yellow solid of mp 229° C. (Found; C, 48.76; H, 2.90; N, 4.46; $C_{13}H_{10}BrNO_4$ requires, C, 48.17; H, 3.11; N, 4.32%).

(d) 2-Acetamido-3-amino-6(7)-methoxynaphtho-1,4-quinone

Dry ammonia was passed for 1 hr. through a stirred, refluxing solution of 2-acetamido-3-bromo-6(7)-methoxynaphtho-1,4-quinone (5.1 g; 0.0158 mole) in nitrobenzene (50 ml) and the cooled solution filtered free of inorganic material and concentrated in vacuo. The red solid which separated was filtered off and washed with ether to give 2.5 g (61%) of material of mp 97° C. (dec).

(e) 4,9-Dihydro-4,9-dioxo-6-methoxy-1H-naphtho[2,3-d]-triazole

To a stirred suspension of 2-acetamido-3-amino-6(7)-methoxynaptho-1,4-quinone (2.5 g; 0.0097 mole) in water (200 ml) was added a solution of sodium dithionite (4 g) in water (20 ml) in one portion. After a further 1 hr. the precipitated hydroquinone was filtered off and suspended in 2 N hydrochloric acid (70 ml) at 0° C. A solution of sodium nitrite (3 g) in water (20 ml) was added over 90 mins. and the mixture stirred overnight. The precipitated triazole was filtered off and recrystallized from acetone/water to give 0.88 g (38%) of derivative of mp 238° C. (dec). (Found; C, 53.40; H, 3.75; N, 17.01; $C_{11}H_7N_3O_3 \cdot H_2O$ requires; C, 53.38; H, 3.67; N, 17.10%).

EXAMPLE 4

4,9-Dihydro-4,9-dioxo-5-nitro-1H-naphtho-[2,3-d]-triazole 4,9-Dihydro-4,9-dioxo-1H-naphtho-[2,3-d]-triazole (5 g, 0.025 mole) was dissolved in a mixture of concentrated sulphuric acid (25 ml) and fuming nitric acid (50 ml). The resulting solution was heated on a steam bath for 10-15 mins and then poured onto ice (250 g). When all the ice had melted the solid was filtered off, washed with water (3×20 ml) and dried to yield a bright yellow solid (4.46 g, 74%), mp 227°-35° (dec). $C^{13}$NMR showed this to consist of a mixture of the 5- and 6-isomers in the approximate ratio 9:1 Multiple recrystallization from acetone and then ethyl acetate yielded a yellow solid, mp 244°-6° (dec) (0.640 g, 10.4%) consisting of the title compound containing <5% of the 6-isomer. (Found; C, 49.47; H, 1.48; N, 22.86; $C_{10}H_4N_4O_4$ requires; C, 49.20; H, 1.64; N, 22.95%).

EXAMPLE 5

(a) 2-Bromo-6-fluoro-3-hydroxynaphtho-1,4-quinone

A solution of bromine (12.5 g), in chloroform (50 ml) was added to a stirred suspension of 6-fluoro-3-hydroxynaphtho-1,4-quinone (12.5 g; 0.065 mole) in chloroform (50 ml) over 15 mins. During the addition the mixture became a clear dark red solution. Stirring was continued for a further 4 hours and a yellow solid which had been deposited as crystals was filtered off, washed with ice-cold chloroform and dried. Yield 13.95 g (80%), mp 183° C. (CHCl₃).

(b) 2-Amino-3-chloro-6(7)-fluoronaphtho-1,4-quinone

A solution of 2-bromo-6-fluoro-3-hydroxynaphtho-1,4-quinone (13.93 g; 0.052 mole) in dry benzene (200 ml) was refluxed with thionyl chloride (6.8 g, 0.057 mole) and D.M.F. (3 drops) for 3 hours. The dark red solution produced was cooled and evaporated to yield an orange solid which was recrystallised from chloroform. Analysis showed this solid to be a mixture of 2,3-dichloro-6-fluoronaphtho-1,4-quinone and 2-bromo-3-chloro-6(7)-fluoronaphtho-1,4-quinone.

Dry ammonia was passed through a stirred solution of the above mixture (5.8 g) in nitrobenzene (75 ml) at room temperature for 3 hours. The mixture was filtered and the dark red filtrate was diluted with anhydrous ether. Dark red crystals were deposited. The crystals were collected, washed with anhydrous ether and dried. Yield 3.5 g mp 167° (d). Mass spec. M+ 224.9991 corresponding to $C_{10}H_5ClNO_2$.

(c) 2-Acetamido-3-chloro-6(7)-fluoronaphtho-1,4-quinone

Concentrated sulphuric acid (2 drops) was added to a suspension of 2-amino-3-chloro-6(7)-fluoronaphtho-1,4-quinone (3.5 g; 0.0155 mole) in acetic anhydride (25 ml). An immediate reaction took place and a yellow crystalline product was formed which was recrystallised from ethyl acetate. Yield 2.1 g (51%); mp 225°-7° (EtOAc).

(d) 2-Acetamido-3-amino-6(7)-fluoronaphtho-1,4-quinone

Dry ammonia was passed for 75 mins. through a stirred solution of 2-acetamido-3-chloro-6(7)-fluoronaphtho-1,4-quinone (2 g; 0.0079 mole) in nitrobenzene (20 ml) at 110° C. A dark red solid crystallised in the mixture. This was filtered off, extracted with chloroform, the extracts were combined and the solvent was evaporated to yield a red solid that was washed with dry ether. The product had mp 218°-220°.

(e) 4,9-Dihydro-4,9-dioxo-6-fluoro-1H-naphtho[2,3-d]-triazole

To a stirred suspension of 2-acetamido-3-amino-6(7)-fluoronaphtho-1,4-quinone (1.0 g, 0.004 mole) in water (150 ml) was added a solution of sodium dithionite (2.5 g) in water (10 ml) in one portion. After a further 1 hour the precipitated hydroquinone was filtered off and suspended in 2 N HCl (50 ml) at 5° C. A solution of sodium nitrite (1.5 q) in water (15 ml) was added over 30 mins. and the mixture stirred overnight. The precipitated triazole was filtered off and recrystallised from acetone/water to give 0.55 g [63%] of derivative of mp 233° (dec), $\nu_{max}$(mull) 1690, 1600 cm⁻¹; M+ 217.0296, $C_{10}H_4FN_3O_2$.

EXAMPLE 6

4,9-Dihydro-6,7-dimethyl-4,9-dioxo-5-nitronaphtho[2,3-d]-triazole 4,9-Dihydro-6,7-dimethyl-4,9-dioxonaphthotriazole (0.4 g, 0.0018 mole) was dissolved in a mixture of concentrated sulphuric acid (4 ml) and fuming nitric acid (8 ml). The solution was heated on a steam bath for two hours and then poured onto ice (200 g). The iced mixture so obtained was left to stand overnight. The resulting solid was filtered off, washed with water (2×50 ml) and dried to give a pale yellow solid (380 mg, 80%) of mp 260°-3°. This was recrystallized from ethanol to yield pale yellow crystals of mp 263°-266° C. (dec), $\nu_{max}$(mull) 3500, 3430, 1690 cm$^{-1}$, δ (DMSO) 2.24 (3H, s); 2.55 (3H, s); 8.18 (1H, s), 1 mid field broad exchangeable proton. (Found; C, 53.10; H, 2.59; N, 20.56; $C_{12}H_8N_4O_4$ requires; C, 52.95; H, 2.96; N, 20.58%).

EXAMPLE 7

(−)-Ephedrine salt of 4,9-Dihydro-6,7-dimethyl-4,9-dioxonaphtho[2,3-d]-ν-triazole A solution of 4,9-dihydro-6,7-dimethyl-4,9-dioxonaphtho[2,3-d]-ν-triazole (454 mg, 0.002 mole) in methanol (20 ml) was added to a solution of (−)-ephedrine (330 mg, 0.002 mole) in methanol (10 ml) in one portion. After standing for 15 mins. the solution remained clear although the colour had darkened. The solvent was removed in vacuo and the brown solid recrystallized from chloroform/petrol (60°-80°) to give 550 mg (63%) of the above named salt, mp 252° C., $\nu_{max}$(mull) 3350-2400 broad, 1665, 1600, 1390, 1260, 980 cm$^{-1}$. δ (DMSO) 0.97 (3H, d); 2.36 (6H, s); 2.54 (1H, quartet); 2.70 (3H, s); 5.14 (1H, d); 7.42 (5H, s); 7.88 (3H, s) and exchangeables. (Found; C, 64.18; H, 6.46; N, 13.28; $C_{22}H_{24}N_4O_3H_2O$ requires; C, 64.45; H, 6.39; N, 13.65%).

EXAMPLE 8

4,9-Dihydro-4,9-dioxo-1H-naphtho[2,3-d]-triazole

A solution of sodium dithionite (2.5 g.) in water (10 ml.) was added to a stirred suspension of 2-acetylamino-3-amino-1,4-naphthoquinone (1.5 g.) in water (150 ml) and the mixture stirred at room temperature until the solid had decolourized (1 hr.). The solid was filtered off, dissolved in water (25 ml.) containing concentrated hydrochloric acid (3 ml), decolourized with charcoal and diluted to 50 ml. by addition of water. A solution of sodium nitrite (10 ml of 10%) was added to cooled (0° C.) stirred solution and after 1 hr. at 0° followed by 2 hrs. at room temperature the precipitated off-white solid was filtered off. Recrystallisation from acetone-water gave 0.62 g. (44%) of the title compound of mp 250° C. (dec) (Lit. mp. 240°-245° C. Fieser and Martin loc. cit.), $\nu$max(mull) 1690 cm$^{-1}$. (Found; C, 60.05; H, 2.81; N, 20.90; $C_{10}H_5N_3O_2$ requires; C, 60.30; H, 2.53; N, 21.01%).

EXAMPLE 9

Ammonium Salt of 4,9-Dihydro-4,9-dioxo-5-nitro-naphtho [2,3-d]triazole 4,9-dihydro-4,9-dioxo-5-nitronaphthotriazole (0.244 g, 0.001 mole) was suspended in ammonia solution (1:1 water/880 ammonia) and warmed on a steam bath for 30 minutes. The mixture became reddish and was cooled to room temperature. The insoluble solid was filtered off and dried to yield 0.21 g (80%) of a pink solid whose NMR spectrum showed it to be the title compound (d$^6$. DMSO, typical 5-substitution pattern multiplet δ 8.0-8.5; broad exchangeable peak 5.7,4H). The compound had no melting point but charred at circa 235° C. (Found; C, 45.51; H, 2.44; N, 26.18; $C_{10}H_7N_5O_4$ requires; C, 45.98; H, 2.70; N, 26.81).

EXAMPLE 10

Sodium Salt of 4,9-Dihydro-6,7-dimethyl-4,9-dioxonaphtho [2,3-d]triazole (a) A suspension of the parent triazole (1.33 g) in water (50 ml) was treated with 2.5 N sodium hydroxide solution until the pH of the solution was 6.5. The resulting yellow solution was filtered and evaporated to dryness. The residual yellowish solid was recrystallized from ethanol to yield a buff solid which turned yellow on drying. Yield 1.433 g mp >360°. Anhydrous material was obtained by drying in vacuum at 110° over phosphorus pentoxide when the material looses its crystallinity (Found; Na: 8.89%, $C_{12}H_8N_3O_2$ Na requires; 9.23%).

(b) 4,9-Dihydro-6,7-dimethyl-4,9-dioxonaphtho[2,3-d]triazole (1.0 g) was suspended in water (50 ml) and the pH brought to 6.8 by the addition of 5 N sodium hydroxide solution. The resulting solution was evaporated to dryness in vacuo. The residue was shaken with ethanol (20 ml) and again evaporated to dryness, this ethanol treatment was repeated. The solid was now dissolved in a minimum of boiling ethanol and the resulting solution cooled to 5° C. A few needles slowly formed, these were filtered off, rinsed with ethanol and dried to yield 0.21 g of bright yellow needles. The NMR spectrum of this material (in d$^6$DMSO) contained a peak corresponding to 10H (after substracting the solvent contribution) which exchanged with D$_2$O. Microanalysis was also consistant with the presence of a pentahydrate (Found: C, 42.91, H, 5.14, N, 12.41, $C_{12}H_8N_3O_2$·Na·5H$_2$O requires C, 42.48, H, 5.35, N, 12.39).

(c) Crude 4,9-dihydro-6,7-dimethyl-4,9-dioxonaphtho [2,3-d]triazole sodium salt was prepared as in (b) above. The residue from evaporation of the solution for the third time was dried at 0.2 mm/Hg for about 5 minutes and then dissolved in the minimum of boiling methanol. On cooling bright yellow needles were deposited from the solution, these were filtered off and dried. NMR suggests these are anhydrous.

PASSIVE CUTANEOUS ANAPHYLAXIS (PCA)

Serum containing heat labile homocytotropic anitbody was raised in rats to crystallized ovalbumin XOA by the method of Mota (I. Mota, Immunology, 7,681 [1964]) using Bordettela pertussis vaccine as adjuvant.

Passive cutaneous anaphylaxis (PCA) was carried out by a method based on that of Ovary and Bier, (A. Ovary and O. G. Bier, Proc. Soc. Exp. Biol. Med. 81, 584, [1952]) as modified by Goose and Blair. (Immunology 16, 749 (1969).

Male Wistar rats of 250–300 g. were given 0.1 ml. of each of six twofold serial dilutions of pooled antiserum in 0.9% saline injected intradermally into separate sites on their shaved backs. Later (72 hrs.) the animals were challenged by intravenous injection of 0.3 ml. of a 1% solution of ovalbumin in an isotonic solution of saline buffered with 0.05 M, pH 7.2, Sorenson Buffer (PBS), mixed with 0.2 ml. of a 5% solution of Pontamine Sky Blue (6BX C.I. 24410, Raymond A. Lamb, London) in isotonic saline. The rats were killed after 20 min and the diameter of the blue wheals at the antibody injection sites was measured on the outer surface of the skin. The starting dilution of the serum was adjusted so that there was no response, after challenge, at the injection site of the highest dilution and a maximum response at the lowest dilutions. Typically six twofold serial dilutions of the serum from ¼ to 1/128 were used.

Compounds were tested for their ability to reduce the diameter of the wheals at those intradermal sites which in control animals gave less than maximum response. Each dose of the compound was administered to six rats at a measured time prior to intravenous challenge with ovalbumin. Control groups of six rats were given the same volume of carrier fluid (0.2 ml, 100 g$^{-1}$) at the same time prior to challenge.

The results were calculated as follows: % inhibition of PCA = 100 (1−a/b) where a = the sum of the diameters of the wheals produced in the test animal at the sites of antibody dilutions as used in control groups and b = the mean sum of the diameters of the wheals produced in the control group of animals at those antibody sites where at least five out of six of the animals gave less than maximum response. A typical variations in the control group of animals was SEM±6%.

| Example | Route | Carrier Fluid | Time* (mins) | Dose mg/kg | % Inhib PCA |
|---------|-------|---------------|--------------|------------|-------------|
| 1(d) | S.C. | PBS | 5 | 0.1 | 30 |
| | | with | 5 | 0.2 | 54 |
| | | NaHCO$_3$ | 5 | 0.4 | 61 |
| | | | 5 | 0.8 | 86 |
| 2(d) | S.C. | PBS | 10 | 20 | 73 |
| | | with NaHCO$_3$ | 30 | 20 | 57 |
| 3(e) | S.C. | PBS with | 10 | 20 | 61 |
| | | NaHCO$_3$ | 30 | 20 | 34 |
| 4 | S.C. | PBS with | 10 | 10 | 44 |
| | | NaHCO$_3$ | 30 | 10 | 19 |
| 5(e) | S.C. | PBS with | 10 | 20 | 90 |
| | | NaHCO$_3$ | 30 | 20 | 27 |
| 6 | S.C. | PBS with | 10 | 1 | 66 |
| | | NaHCO$_3$ | 30 | 1 | 28 |
| 8 | S.C. | PBS with | 5 | 1 | 39 |
| | | NaHCO$_3$ | 5 | 2 | 82 |

Acute toxicity: no toxic symptoms were observed with any of the compounds while carrying out the tests described above.

Toxicity: Oral LD$_{50}$ of the compound of example 1(d) in Charles River Sprage Dawley CD strain Male Rats: 980 mgkg$^{-1}$. LD$_{50}$ data confidence limits: 95%, 548–1,413 mgkg$^{-1}$.

What we claim is:

1. A method of inhibiting an antigen induced allergic response which comprises prophylactically administering to a patient in need thereof an effective dose of a compound of the formula:

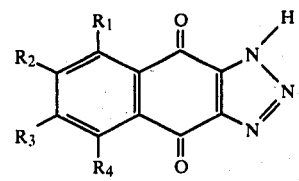

or a pharmaceutically acceptable salt thereof wherein R$_1$, R$_2$, R$_3$ and R$_4$ are the same or different group selected from the group consisting of hydrogen, halo, nitro, lower alkyl or lower alkoxy, or any adjacent two of R$_1$ to R$_4$ together are alkylene of 3 to 5 carbon atoms or 1,4-buta-1,3-dienylene.

2. A pharmaceutical composition for prophylactically inhibiting an antigen induced allergic response which comprises in metered aerosol or a solid orally administered form an effective amount of a compound of the formula:

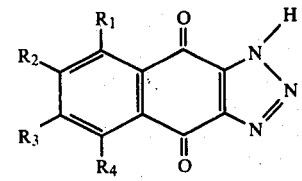

wherein R$_1$, R$_2$, R$_3$ and R$_4$ are the same or different group selected from the group consisting of hydrogen, halo, nitro, lower alkyl or lower alkoxy, or any adjacent two of R$_1$ to R$_4$ together are alkylene of 3 to 5 carbon atoms of 1,4-buta-1,3-dienylene, or a pharmaceutically acceptable salt thereof in such purity as to permit medicinal administration and a pharmaceutically acceptable carrier.

3. 4,9-dihydro-6,7-dimethyl-4,9-dioxo-1H-naphtho[2,3-d]-triazole or a pharmaceutically acceptable salt thereof.

4. 4,9-dihydro-6,7-dimethyl-4,9-dioxo-1H-naphtho[2,3-d]-triazole sodium salt.

5. 4,9-dihydro-6,7-dimethyl-4,9-dioxo-1H-naphtho[2,3-d]-triazole (−)-ephedrine salt.

* * * * *